United States Patent [19]

Smith

[11] 4,307,072

[45] Dec. 22, 1981

[54] N-TRIIODOBENZOYLAMINOACYL POLYHYDROXIC AMINES

[75] Inventor: Kenneth R. Smith, Florissant, Mo.

[73] Assignee: Mallinckrodt, Inc., St. Louis, Mo.

[21] Appl. No.: 817,071

[22] Filed: Jul. 19, 1977

Related U.S. Application Data

[63] Continuation of Ser. No. 666,389, Mar. 12, 1976, abandoned.

[51] Int. Cl.$^3$ .................. H61K 29/02; C07C 127/19; C07C 103/78
[52] U.S. Cl. ......................................... 424/5; 564/51; 564/59; 564/99; 564/153; 564/156; 564/157; 564/158; 564/164; 564/165; 564/167; 564/169; 564/170; 564/175; 564/176; 564/177
[58] Field of Search .......... 260/558 A, 558 D, 553 A, 260/556 A, 559 A; 424/5

[56] References Cited

U.S. PATENT DOCUMENTS

| | | | |
|---|---|---|---|
| 2,939,881 | 6/1960 | Wiegert | 424/5 X |
| 3,073,814 | 1/1963 | Wiegert et al. | 424/5 X |
| 3,145,197 | 8/1964 | Hoey | 424/5 X |
| 3,701,771 | 10/1972 | Almen et al. | 424/5 X |
| 3,953,501 | 4/1976 | Klieger et al. | 260/558 A |

*Primary Examiner*—Natalie Trousof
*Assistant Examiner*—Vera C. Clarke
*Attorney, Agent, or Firm*—Senniger, Powers, Leavitt and Roedel

[57] ABSTRACT

Nonionic triiodobenzoyl amino acyl derivatives of polyhydroxy amines. Such amines are useful as non-ionic X-ray contrast agents. For Example 2-(3-acetamido-2,4,6-triiodo-5-N-methylacetamidobenzoyl glycylamino)-2-deoxy-D-glucitol is especially useful in angiography.

37 Claims, No Drawings

N-TRIIODOBENZOYLAMINOACYL POLYHYDROXIC AMINES

This is a continuation, of application Ser. No. 666,389, filed Mar. 12, 1976, now abandoned.

BACKGROUND OF THE INVENTION

This invention relates to certain N-triiodobenzoylaminoacyl polyhydroxic amines that are useful as nonionic X-ray contrast agents. It is also related to the radiological compositions and to the use of such compositions.

DESCRIPTION OF THE PRIOR ART

More recently, Almen et al (U.S. Pat. No. 3,701,771, dated Oct. 31, 1972) have disclosed certain nonionic N-(2,4,6-triiodobenzoyl)-sugar amines which are stated to be useful as X-ray contrast agents in the cerebrospinal cavities. In these compounds, a polyhydroxyalkyl chain is coupled to an iodoaromatic moiety in order to impart water solubility without resorting to ionic species.

Certain of the nonionic compounds disclosed in this patent were reported to be highly soluble in water while others were reported to have a medium or low water solubility.

An older known X-ray contrast agent is 2-iodohippuric acid sodium salt. This compound is referred to in *Medical Radiography and Photography*, Volume 40, Supplement 1964.

Presently, no triiodohippuric acids or derivatives are used as X-ray contrast agents. However, several ionic compounds based on triiodohippuric acid have been reported. In Offenlegungsschrift No. 2,207,950, Feb. 16, 1972, and in *European Journal of Medicinal Chemistry—Chimica Therapeutica*, 10, 84, 1975, compounds of the general structure 1 and 2 are reported:

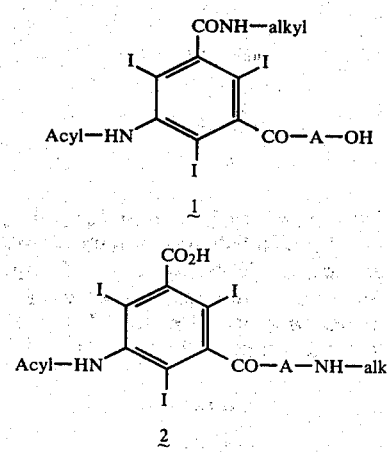

where A=aminoacyl residue.

Others are disclosed in British Pat. No. 867,880 and H. Suter and H. Zutter, *Helv. Chim. Acta.*, Volume 54, Page 2551, (1971).

In certain instances nonionic X-ray contrast media have been found to be less toxic than their ionic counterparts. This is believed to be due at least in part to the fact that nonionic compounds, being substantially non-ionized in aqueous solution, create less of an osmatic inbalance than do ionic compounds, i.e., nonionic X-ray contrast media contribute only one molecular species per iodinated moiety as compared to ionic X-ray contrast media which contribute two or more species per iodinated moiety.

An interest has developed, therefore, in the synthesis of water-soluble nonionic X-ray contrast media possessing low toxicity and high iodine content for use in the X-ray visualization of areas of the body such as, for example, the cardiovascular and central nervous system where high concentrations of contrast media are required to provide sufficient opacity.

BRIEF DESCRIPTION OF THE INVENTION

In accordance with this invention compounds represented by the following formula are useful as nonionic X-ray contrast agents

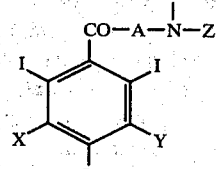

Formula I wherein X and Y are each nonionic functions compatible with low toxicity and/or water solubility in the 2,4,6-triiodo configuration, A is an amino substituted lower alkanoic acid coupler and

is a monovalent residue of a polyhydroxy amine, wherein N is a nitrogen atom, R is hydrogen, lower alkyl, hydroxy-lower alkyl or polyhydroxy lower alkyl, Z is polyhydroxy lower alkyl or oxo, polyhydroxy lower alkyl.

Another embodiment of this invention is directed to a radiological composition containing at least one of the nonionic compounds described above as the X-ray contrast agent together with a pharmaceutically acceptable vehicle.

Another embodiment of this invention is directed to the use of the radiological composition in an X-ray visualization method.

Certain of the above mentioned compounds are advantageous in that they are 100% w/v soluble in water at 25° C. Such solutions are particularly useful in various types of angiography owing to the high concentration of iodine that can be obtained. The high concentration provides a solution which is satisfactory for visualization.

DETAILED DESCRIPTION OF THE INVENTION

The term "amino substituted lower alkanoic acid coupler" as used herein includes straight and branched chain alkanoic acids of up to 12 carbon atoms inclusive substituted with an amino group, on the amino portion of such coupler is the substituted benzoyl moiety and on the acyl portion is the polyhydroxy amine. One of the amino hydrogens on the amino group may be further substituted with a lower alkyl, hydroxy lower alkyl or polyhydroxy lower alkyl.

Examples of amino substituted lower alkanoic acid couplers include those derived from aliphatic amino acids including glycine, alanine, serine, threonine, valine, leucine, isoleucine; aromatic amino acids, such as phenylalanine, tyrosine; sulfur containing amino acids, such as cysteine, cystine, methionine; heterocyclic amino acids, such as tryptophan, proline, hydroxyproline and others such as histadine, lycine and arginine. Because of ease and convenience glycine is preferred.

The term "lower alkyl" as used herein includes straight and branched chain radicals of up to 8 carbon atoms inclusive and is exemplified by methyl, ethyl, propyl, butyl, pentyl, hexyl, heptyl and octyl. The term "hydroxy lower alkyl" as used herein includes straight and branched chain radicals of up to 8 carbon atoms substituted with one hydroxy group and is exemplified by hydroxy ethyl, hydroxy propyl, hydroxy butyl, hydroxy pentyl, hydroxy hexyl and hydroxy octyl. Preferably, the carbon atom linked to the nitrogen is not substituted with the hydroxy group. The term "polyhydroxy lower alkyl" includes straight and branched chain radicals of up to 8 carbon atoms substituted with 2 to 8 hydroxy groups. It does not include radicals that have 2 or more hydroxy groups substituted on one carbon atom. Preferably, the carbon atom linked to the nitrogen is not substituted with a hydroxy group. Examples include 2,3-dihydroxypropyl, 2,3,4-trihydroxybutyl, 2,3,4,5,6-pentahydroxyhexyl, and 2,3,4-trihydroxyoctyl. The term "oxo polyhydroxy-lower alkyl" includes straight, branched, and cyclic radicals of up to 8 carbon atoms substituted with one oxygen atom (=O) and 2 to 6 hydroxy groups. This term does not include radicals that have 2 or more hydroxy groups substituted on one carbon atom; that have the oxygen atom substituted on the carbon linked to the nitrogen; and that ionize, i.e., those that have a hydroxy group and oxygen atom on the same carbon atom. Preferably, the carbon atom linked to the nitrogen is not substituted with a hydroxy group. Examples of oxo polyhydroxy-lower alkyl include 3,4-dihydroxy-2-oxo-butyl; 2,4,5-trihydroxy-3-oxo-pentyl; 3,4,5,6-tetrahydroxy-2-oxo-hexyl, etc.

The radical R and Z in the above Formula I, as stated in the foregoing are inclusive of such groups as lower alkyl, hydroxy lower alkyl and polyhydroxy lower alkyl and oxopolyhydroxy lower alkyl, and are preferably although not necessarily radicals of a solely hydrocarbon, hydroxy hydrocarbon or oxohydroxy hydrocarbon nature.

Preferably

is the monovalent residue of aldosamines, N-(lower alkyl) aldosamines, ketosamines, N-(lower alkyl) ketosamines, N-(polyhydroxy-lower alkyl) amines, N-alkyl-N-(polyhydroxy-lower alkyl) amines, and deoxyaldosamines.

Aldosamines include those of the formula:

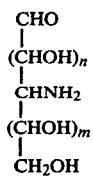

where m=0 to 4, n=0 to 4, and the sum of m+n=0 to 4, and include amines such as D-erythrosamine, D-glucosamine (2-amino-2-deoxy-D-glucose), D-galactosamine and various other tetrosamines, pentosamines, hexosamines and heptosamines. Other amines of this type include 2-amino-2-deoxy-D-galactose, 2-amino-2-deoxy-D-mannose, 2-amino-2-deoxy-D-talose, 2-amino-2-deoxy-D-glucose, etc. Lower alkyl aldosamines include those of the formula;

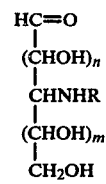

where m=0 to 4, n=0 to 4, and the sum of m+n=0 to 4 and R is lower alkyl may also be employed. These amines include N-methyl-D-glucosamine (2-methylamino-2-deoxy-D-glucose), N-methyl-D-galactosamine, 3-methylamino-3-deoxy-D-xylose, 4-ethylamino-4-deoxy-D-galactose, etc.

Ketosamines include those of the formula:

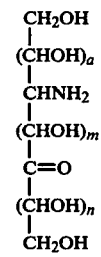

where a=0 to 4, m=0 to 4, n=0 to 4 and the sum of a+m+n=0 to 4 and include amines such as D-ribulosamine, D-sorbosamine, D-fructosamine, D-gluco-heptulosamine and various other pentulosamines, hexulosamines and heptulosamines. Similarly, N-(lower alkyl) ketosamines include those of the formula:

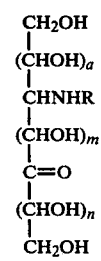

where a=0 to 4, m=0 to 4, the sum of a+m+n=0 to 4 and R=lower alkyl and include amines such as N-methyl-D-sorbosamine, N-methyl-D-fructosamine, etc.

Ketosamines include those of the formula:

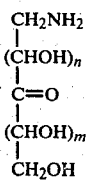

where n=0 to 4, n=0 to 4 and the sum of n+m=0 to 4 and include 1-amino-1-deoxy-D-fructose. Similarly, N-(lower alkyl) ketosamines include those of the formula

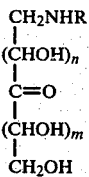

where n=0 to 4, m=0 to 4, R=lower alkyl and the sum of n+m=0 to 4 and include 1-hydroxy-3-methylamino-2-propanone.

N-(polyhydroxy-lower alkyl) amines include those of the formula:

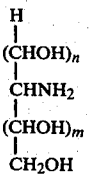

where n=0-5, m=0-5 and the sum of n+m=0-5 and include such amines as 2-amino-2-deoxy glucitol, and 1-amino-1-deoxy-sorbitol, etc. Other amines of this type include 1-amino-1-deoxy-D-glycero-D-gulo-heptitol, 1-amino-1-deoxy-glycero-D-galacto-heptitol, 1-amino-1-deoxy-D-glycero-1-manno-heptitol, 1-amino-1-deoxy-D-arabitol, 1-aminodeoxy-D-glucitol.

N-lower alkyl-N-(polyhydroxy-lower alkyl) amines include those of the formula:

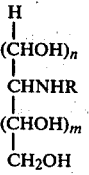

where n=0-2, m=1-5 and the sum of m+n=1-5, and R is lower alkyl or hydroxy lower alkyl and specifically include 1-deoxy-1-methylamino-sorbitol, 1-deoxy-1-ethylamino-sorbitol, 1-ethylamino 1-deoxy-D-arabitol, 1-methylamino-2,3-propanediol, 2-methylamino-1,3-propanediol, 3-ethylamino-3-deoxy-D-arabitol and 1-deoxy-1-methylamino-D-glucitol (N-methylglucamine), and secondary amines such as diethanol amine and dipropanolamine.

Deoxy-aldosamines which may be the source of the monovalent residue of a polyhydroxy-amine include the 1-deoxy compounds of the formula:

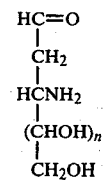

where n=1 to 3 and the corresponding 3-deoxyaldosamines and the 4-deoxy aldosamines.

Lower alkyl-glycosidoamines also may be used and include those of the formula:

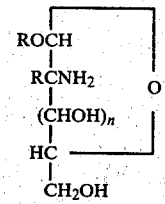

where n=1 to 3 and R is lower alkyl and include compounds such as methyl-glucosidoamine, methyl-gulosidoamine, etc.

Polyhydroxy-carbocyclic amines are useful in the practice of the invention and include compounds such as 1-amino-2,3,4,5,6-pentahydroxycyclohexane, 1-amino-2,3,4,5-tetrahydroxycyclopentanes, etc. Similarly, the lower alkyl-(polyhydroxy-carbocyclic) amines may be 1-N-methylamino-2,3,4,5,6-pentahydroxycyclohexanes, 1-N-methylamino-2,3,4,5-tetrahydroxycyclopentanes, etc.

The substituents in the 3- and 5-positions of the ring, namely X and Y, are nonionizing functions compatible with low toxicity and/or solubility in the 2,4,6-triiodophenyl configuration. As is known by those skilled in the art, the term "detoxifying and/or solubilizing groups" has been used as a generic designation for a substantial number of functional groups whose occurrence in the meta-position(s) in a 2,4,6-triiodinated moiety has come to be associated with compounds which exhibit a relatively low toxicity and/or a relatively high water solubility (cf. G. B. Hoey, P. E. Wiegert and R. D. Rands, Jr., "Organic Iodine Compounds as X-Ray Contrast Media;," in *International Encyclopedia of Pharmacology and Therapeutics*, Section 76, "Radiocontrast Agents," P. K. Knoefel, Section Editor, Pergamon Press: Vol. 1, pp. 23-40, 54-73 (1971). While the use of such terminology originated in connection with 2,4,6-triiodobenzoic acid derivatives possessing relatively low toxicity and/or relatively high water solubility, the results set forth herein are consistent with the view that substantially the same nonionizing functions are also compatible with low toxicity and/or water solubility in the triiodinated moiety of the nonionic compounds of the present invention.

Among the nonionizing functions which may constitute X and Y may be mentioned the following: lower alkoxy, e.g., methoxy and ethoxy; hydroxy-(lower alkoxy), e.g., 2-hydroxy-ethoxy; lower alkoxy-(lower alkoxy), e.g., methoxy-ethoxy and ethoxy-propoxy; lower acylamino, e.g., acetamido and propionamido; lower acylamino (lower alkyl), e.g., acetamidomethyl and acetamidoethyl; lower acylamino-(lower acylamino), e.g., aceturamido; hydroxy-lower acylamino, e.g., hydroxyacetamido and hydroxypropionamido; N-(lower alkyl)-lower acylamino, e.g., N-methylacetamido and N-methylpropionamido; lower alkylsulfonamido, e.g., methylsulfonamido and ethylsulfonamido; N-(lower alkyl)-lower alkylsulfonamido, e.g., N-methyl-ethylsulfonamido and N-ethyl-methylsulfonamido; 3,3-bis (lower alkyl)-ureido, e.g., 3,3-dimethylureido and 3-methyl-3-ethylureido; lower perfluoroacylamino, e.g., perfluoroacetamido and perfluoropropionamido; carbamyl; N-(lower alkyl) carbamyl, e.g., N-methylcarbamyl and N-ethylcarbamyl; N-(hydroxy lower alkyl) carbamyl, e.g., N-(2-hydroxyethyl) carbamyl and N-(3-hydroxypropyl) carbamyl; N-(polyhydroxy lower alkyl) carbamyl, e.g., N-(2,3-dihydroxypropyl) carbamyl and N-(2,3,4-trihydroxybutyl) carbamyl, N,N-di-(lower alkyl) carbamyl, e.g., N,N-dimethylcarbamyl and N,N-diethylcarbamyl; N,N-bis-(hydroxy lower alkyl) carbamyl, e.g., N,N-bis-(2-hydroxyethyl) carbamyl; N,N-bis-(polyhydroxy lower alkyl) carbamyl, e.g., N,N-bis-(2,3-dihydroxypropyl) carbamyl; lower alkoxy-(lower acyl-amino), e.g., methoxy-acetamido and ethoxy-acetamido; lower alkoxy-alkoxy-(lower acylamino), e.g., methoxyethoxy-acetamido; hydroxy and hydroxy-lower alkyl, e.g., hydroxymethyl and hydroxyethyl. As used above, the term "lower" (e.g., lower alkyl and lower alkoxy) means that the function contains between 1 and 8 carbon atoms. Those skilled in the art will recognize that functions of the above type other than those specifically enumerated may also constitute X and Y.

In another aspect of the invention, one of X and Y may be constituted by hydrogen or one of the functions enumerated above and the other of X and Y may be constituted by the function

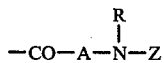

wherein A, R and Z have the same significance as previously described.

REPRESENTATIVE COMPOUNDS OF THIS INVENTION 2-(3-acetamido-2,4,6-triiodo-5-N-methylacetamidobenzoylglycylamino)-2-deoxy-D-glucitol 2-(3-acetamido-2,4,6-triiodo-5-N-methylcarbamylbenzoylglycylamino)-2-deoxy-D-glucitol.

1-(3-acetamido-2,4,6-triiodo-5-N-methylacetamidobenzoylglycylamino)-1-deoxy-D-glucitol.

2-(3-acetamido-2,4,6-triiodo-5-N-methylacetamidobenzoyl-L-ananylamino)-2-deoxy-D-mannitol.

3-(3,5-diacetamido-2,4,6-triiodo-benzoyl-L-phenylalanylamino)-3-deoxy-D-galactitol.

2-(3-acetamido-2,4,6-triiodo-5-N-methylacetamidobenzoylglycylamino)-2-deoxy-D-glucose.

2-(3-butyrylamino-2,4,6-triiodo-5-N-ethylacetamidobenzoyl-L-valinyl)-2-deoxy-D-galactose 6-(3-acetamido-2,4,6-triiodo-5-N-propylacetamidobenzoyl-L-leucinyl)-6-deoxy-D-fructose (5-acetamido-2,4,6-triiodoisophthaloyl)-N,N'-bis-2,3,-dihydroxypropyl-N,N'-dimethyl-bis-glycinamide (5-acetamido-2,4,6-triiodoisophthaloyl)-N,N'-bis-2-hydroxyethyl-N,N'-dimethyl-bis-glycinamide 5-propionylamino-N,N'-bis-2,3-dihydroxypropyl-2,4,6-triiodoisophthaloyl)-alaninamide The novel compounds of this invention and mixtures thereof may be used as X-ray contrast agents in various radiographic procedures including those involving cardiovascular visualization, coronary arteriography, aortography, cerebral and peripheral angiography, myelography, ventriculography, arthrography, cholangiography, intravenous pyelography, urography and bronchography. Certain compounds of the invention exhibit high water solubility and relatively low toxicity while others may exhibit the limited water solubility and relatively low toxicity required for example, in oral radiographic procedures or as powders for bronchography. 2-(3-Acetamido-2,4,6-triiodo-5-N-methylacetamdiobenzoylglycylamino)-2-deoxy-D-glucitol is especially useful in angiography because it is 100% soluble, consequently it may be given in small volumes but still providing adequate iodine for imaging.

Isomeric mixtures of the compounds of this invention may be used as X-ray contrast agents. Generally, the amount of each isomer contained in the mixture may vary over a wide range provided that the mixture functions as a satisfactory X-ray contrast agent.

A further feature of the present invention is a radiological composition containing at least one nonionic compound according to the invention as an X-ray contrast agent together with a pharmaceutically acceptable vehicle.

Vehicles include those that are suitable for injection such as aqueous buffer solutions, sterile water for injection, physiological saline, and balanced ionic solutions containing chloride and/or bicarbonate salts of normal blood plasma cations such as Ca, Na, K and Mg.

The concentration of one of the compounds of this invention in the pharmaceutically acceptable vehicle, for example, an aqueous medium, varies with the particular field of use. A sufficient amount is present to provide satisfactory X-ray visualization. For example, when using aqueous solutions lower concentrations are required for ventriculography, myelography and radiculography than for angiocardiography. The preferred concentration and dosage ranges of the compounds in aqueous solutions for these three applications are as follows:

| | Concentration mg/I/ml. | Dose ml. |
|---|---|---|
| Myelography | 150–300 | 5–12 |
| Cardiovascular | 300–580 | 5–100 |
| Urography | 140–400 | 25–300 |

The radiological composition is administered so that the contrast agent remains in the system for about 2 to 3 hours, although both shorter and longer residence periods are normally acceptable. The compounds of this invention may thus be formulated for cerebrospinal visualization conveniently in vials or ampoules containing 5 to 15 ml. of an aqueous solution thereof, but for vascular visualization larger quantities, e.g., 10 to 500 ml. will be given. They may also be formulated and lyophilized to a powder.

The radiological compositions may be used in the usual way in X-ray procedures. For example in the case of cardiovascular visualization, a sufficient amount of the radiological composition to provide adequate visualization is injected into the cardiovascular system and then the cardiovascular agent is scanned with a suitable machine, for example a fluoroscope.

The new compounds according to the invention can be prepared in any convenient way.

Compounds of Formula I may be prepared by the following method.

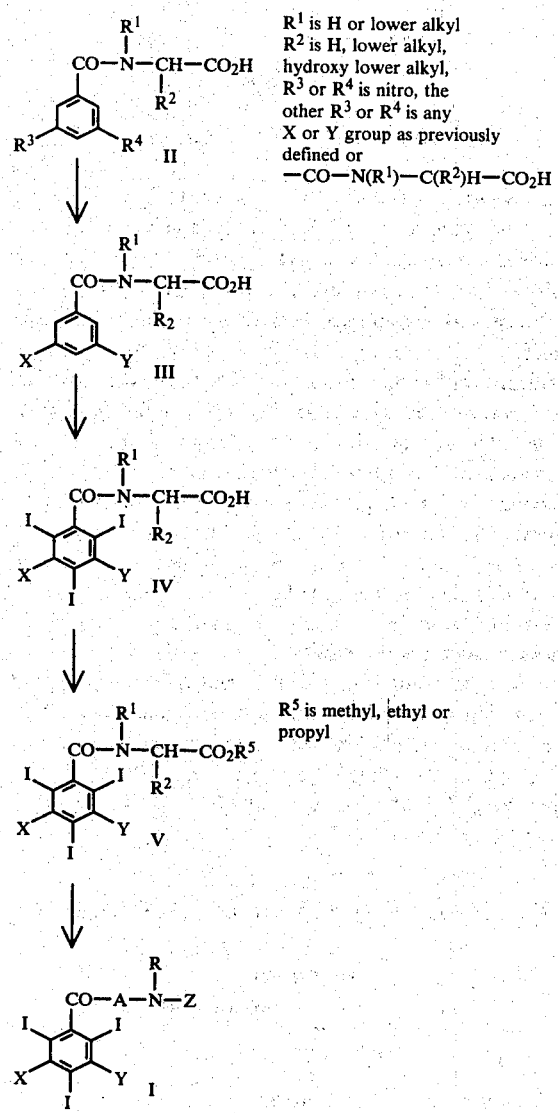

$R^1$ is H or lower alkyl
$R^2$ is H, lower alkyl, hydroxy lower alkyl,
$R^3$ or $R^4$ is nitro, the other $R^3$ or $R^4$ is any X or Y group as previously defined or
—CO—N($R^1$)—C($R^2$)H—CO$_2$H $R^5$ is methyl, ethyl or propyl Formula II compounds wherein one of the $R^3$ or $R^4$ groups is —CON($R^1$)CH($R^2$)CO$_2$H may be prepared by the method described in "Practical Organic Chemistry," A. I. Vogel, pp. 436–437, John Wiley & Sons Inc., New York, New York (1966). They are converted to Formula III compounds by catalytic reduction with a nobel metal catalyst such as palladium or platinum in a suitable solvent such as methanol, ethanol, or water. When using water as the solvent, Formula II compounds are converted to an alkali metal salt with an alkali metal hydroxide. Typically the ratio of solvent to Formula II compound or an alkali metal salt thereof is from about 1:1 to 500:1. The reaction proceeds at room temperature and is complete in about two hours, however, the temperature may range from 10° to 150° C. and the time for reduction may range from 1 to 4 hours. Any suitable pressure may be used, e.g., 15 to 100 psi. Generally, sufficient catalyst is employed to reduce the Formula II compound or alkali metal salt thereof. Typically, about 0.01 to 1 part by weight of catalyst is used for each part by weight of Formula II compound or salt thereof. After completion of the reaction the reaction mixture is filtered to remove the catalyst and is then used to prepare Formula IV compounds.

Formula IV compounds are prepared by iodinating Formula III compounds. First the solution containing a Formula III compound is acidified to pH 1 with a suitable acid such as hydrochloric. Initially the temperature is maintained at 40° to 50° C., after addition of the iodinating agent, it is permitted to rise to 50° to 80° C. and heating is continued until iodination is complete, usually 3 to 6 hours. Generally, 3 to 4 molar equivalents of the iodinating agent, e.g., iodine monochloride is used for each mole of Formula III compounds. The iodinated compounds are recovered by filtration and purified.

Alternatively, Formula IV compounds can be prepared from 5-nitroisophthalic acid using the procedure described in German Offen. No. 2,207,950.

Alternatively, Formula IV compounds derived from 3,5-dinitrobenzoic acid can be prepared using the same general reduction and iodination conditions mentioned above with respect to Formula II compounds wherein one of $R_3$ or $R_4$ is —CO N($R^1$)CH($R^2$)CO$_2$H.

Formula IV compounds where one of the groups is an acyl amino may be alkylated with an alkylating agent in a suitable solvent such as water, methanol or ethanol and with sufficient base, generally 4 to 6 molar equivalents per mole of Formula IV compound. Any suitable base such as sodium hydroxide, sodium ethoxide or sodium methoxide may be used. Suitable alkylating agents include alkyl halides, such as methyl iodide, ethyl chloride, propyl bromide etc., or dialkyl sulfates such as dimethyl sulfate or diethyl sulfate. The alkylation proceeds at 50° C. and is completed normally in about 1 to 5 hours. However, the temperature may range from 40° to 60° C. The product is isolated in the usual manner, for example, by dissolving in aqueous sodium hydroxide and precipitating with hydrochloric acid.

Formula IV compounds wherein X is an amino group may also be acylated with an acyl anhydride. Typically about 4 to 6 weights of acyl anhydride and 0.01 to 1 weight of sulfuric acid is used for each weight of Formula IV compound. The reaction temperature may vary from 20° to 60° C., typically 30° C. The reaction is completed in 5 to 20 hours usually about 8 hours. The product is recovered in the usual manner by filtration.

Formula V compounds are prepared by esterifying Formula IV compounds with the appropriate alcohol. Usually a mineral acid such as sulfuric is used as a catalyst in catalytic amounts, i.e., 1% by weight of the Formula IV compound present. Typically about 10 parts by weight of the alcohol is used for each part by weight of the Formula IV compound. The Formula V compounds are isolated in the usual manner, i.e., by cooling and collecting the crystallized solids.

Formula I compounds are then prepared by refluxing the Formula V compound in a suitable solvent, e.g., methanol, if necessary and a polyhydroxyamine. Typically 1 to 3 parts by weight of the polyhydroxyamine and 5 to 7 parts by weight of the solvent is utilized for each part by weight of the Formula V compound. The polyhydroxyamine may also act as a solvent, and then more would be used. Typically 6 to 10 parts by weight per part by weight of Formula V compound is used. Formula I compounds may be recovered in any suitable manner.

Alternatively, compounds of Formula I may be prepared by the following method:

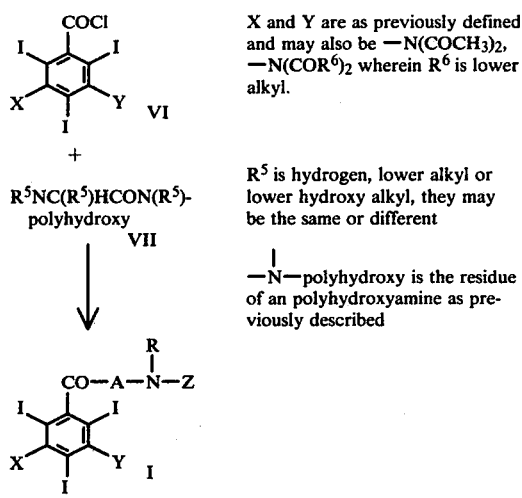

X and Y are as previously defined and may also be —N(COCH$_3$)$_2$, —N(COR$^6$)$_2$ wherein R$^6$ is lower alkyl.

R$^5$ is hydrogen, lower alkyl or lower hydroxy alkyl, they may be the same or different —N—polyhydroxy is the residue of an polyhydroxyamine as previously described Compounds of Formula VI are prepared according to German Pat. No. 2,031,724; Formula VII compounds are prepared according to Liefländer, Hoppe-Seyler's Z. Physicol Chem., 348, 363–70 (1967); and the reaction of VI and VII to form Formula I compound is carried out according to the general method in German Pat. No. 2,031,724.

EXAMPLES

The invention will now be illustrated by the following examples. Temperatures are in degrees C.

EXAMPLE 1

Preparation of 2-(3-Acetamido-2,4,6-triiodo-5-N-methylacetamidobenzoylglycylamino)-2-deoxy-D-glucitol A. Preparation of 2-Acetamido-2-deoxy-D-glucitol

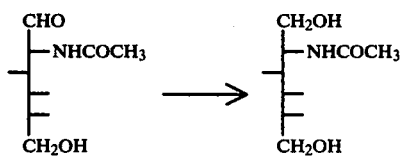

A solution of 100 g. (0.45 mole) of N-acetyl-D-glucosamine in 300 ml. of water was cooled to 15° and a solution of 16 g. of sodium borohydride in 300 ml. of water was added dropwise. During the addition the temperature was held below 50° by addition of ice. After the addition the mixture was stirred for 40 min., cooled to 10° and the excess hydride decomposed by addition of 102 ml. (0.58 mole) of acetic acid. The solution was poured into 550 ml. of prewashed Amberlite 120 resin (H+ form) (0.96 mole @ 1.75 meq/ml.) and stirred for 15 min. The resin was removed by filtration and washed with water. The combined filtrate and wash were evaporated to dryness. The residue was dissolved in 1 l of hot 2β-ethanol, evaporated to 700 ml. and stirred overnight. 90 g. (90%) of product was isolated. The melting point of the product was 153°–154° (lit 153°) and was shown to be pure by tlc (silica gel plate—ethanol/concentrated ammonia 50:50-methanolic sulfuric acid spray and heat development)

B. Preparation of 2-Amino-2-Deoxy-D-Glucitol Hydrochloride

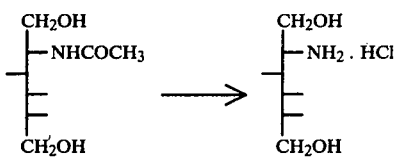

A solution of 90 g. (0.40 mole) of 2-acetamido-2-deoxy-D-glucitol in 1.4 l of water and 0.6 l of conc. hydrochloride acid was heated at 90° for 6 hrs. and allowed to stand overnight at room temperature. The solution was evaporated at aspirator pressure to approximately 1 l. Ethanol was added to the solution in 100 ml. portions and evaporation was continued; the addition and evaporation were repeated until crystals appeared. The solution was allowed to stand for 3 hrs. at room temperature and filtered to furnish 68 g. of product. A second portion 10 g. was isolated from the mother liquor. The melting point of first and second portions were 161° and 160° (lit. 160–161). Both crops were shown to be pure by tlc (silica gel plate—ethanol/concentrated ammonia 50:50—ninhydrin and methanolic sulfuric acid development).

The free 2-amino-2-deoxy-D-glucitol was prepared by stirring 78 g. of the hydrochloride in a mixture of 400 ml. of ethanol and 83 ml. of diethylamine for two days. The solids were filtered and washed with ethanol to give 62 g. (95%) melting point 129°–130° (lit. melting point 131).

C. Preparation of 2-(N-Carbobenzyloxyglycylamino)-2-deoxy-D-glucitol

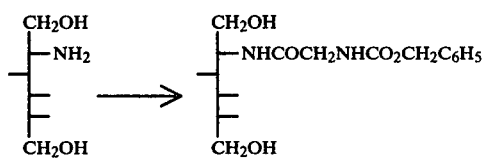

A mixture of 275 ml. of dry tetrahydrofuran and 275 ml. of dry dioxane was cooled to −5° and 12.88 ml. (9.35 g., 0.092 mole) of triethylamine, 8.74 ml. (9.96 g., 0.092 mole) of ethyl chloroformate and 19.23 g. (0.092 mole) of N-carbobenzyloxyglycine were added. The mixture was stirred for 15 min. at −5° and then a cold (0°–5°) solution of 16.65 g. (0.092 mole) of 2-amino-2-deoxy-D-glucitol in 40 ml. of water was added in one portion. The cooling bath was removed and the mixture was allowed to stir at ambient temperature for four hours. The solvent was evaporated in vacuum at 30°–40° and the residue was stirred overnight with 500 ml. of ethanol. Filtration furnished 30 g. of a solid. The solid was recrystallized from 700 ml. of methanol to give 21 g. of product. Tlc shows the product to be pure (silica gel plate—benzene/methyl ketone/88% formic acid 60:25:25—methanolic sulfuric acid development).

The new compounds according to the invention can be prepared in any convenient way.

Compounds of Formula I may be prepared by the following method.

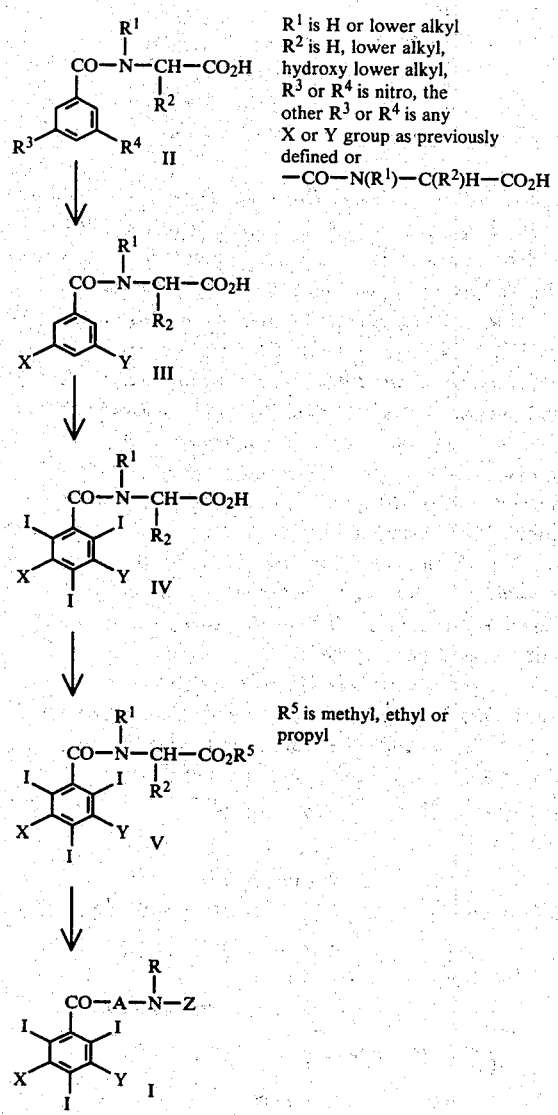

Formula II compounds wherein one of the $R^3$ or $R^4$ groups is $-CON(R^1)CH(R^2)CO_2H$ may be prepared by the method described in "Practical Organic Chemistry," A. I. Vogel, pp. 436-437, John Wiley & Sons Inc., New York, New York (1966). They are converted to Formula III compounds by catalytic reduction with a nobel metal catalyst such as palladium or platinum in a suitable solvent such as methanol, ethanol, or water. When using water as the solvent, Formula II compounds are converted to an alkali metal salt with an alkali metal hydroxide. Typically the ratio of solvent to Formula II compound or an alkali metal salt thereof is from about 1:1 to 500:1. The reaction proceeds at room temperature and is complete in about two hours, however, the temperature may range from 10° to 150° C. and the time for reduction may range from 1 to 4 hours. Any suitable pressure may be used, e.g., 15 to 100 psi. Generally, sufficient catalyst is employed to reduce the Formula II compound or alkali metal salt thereof. Typically, about 0.01 to 1 part by weight of catalyst is used for each part by weight of Formula II compound or salt thereof. After completion of the reaction the reaction mixture is filtered to remove the catalyst and is then used to prepare Formula IV compounds.

Formula IV compounds are prepared by iodinating Formula III compounds. First the solution containing a Formula III compound is acidified to pH 1 with a suitable acid such as hydrochloric. Initially the temperature is maintained at 40° to 50° C., after addition of the iodinating agent, it is permitted to rise to 50° to 80° C. and heating is continued until iodination is complete, usually 3 to 6 hours. Generally, 3 to 4 molar equivalents of the iodinating agent, e.g., iodine monochloride is used for each mole of Formula III compounds. The iodinated compounds are recovered by filtration and purified.

Alternatively, Formula IV compounds can be prepared from 5-nitroisophthalic acid using the procedure described in German Offen. No. 2,207,950.

Alternatively, Formula IV compounds derived from 3,5-dinitrobenzoic acid can be prepared using the same general reduction and iodination conditions mentioned above with respect to Formula II compounds wherein one of $R_3$ or $R_4$ is $-CO\ N(R^1)CH(R^2)CO_2H$.

Formula IV compounds where one of the groups is an acyl amino may be alkylated with an alkylating agent in a suitable solvent such as water, methanol or ethanol and with sufficient base, generally 4 to 6 molar equivalents per mole of Formula IV compound. Any suitable base such as sodium hydroxide, sodium ethoxide or sodium methoxide may be used. Suitable alkylating agents include alkyl halides, such as methyl iodide, ethyl chloride, propyl bromide etc., or dialkyl sulfates such as dimethyl sulfate or diethyl sulfate. The alkylation proceeds at 50° C. and is completed normally in about 1 to 5 hours. However, the temperature may range from 40° to 60° C. The product is isolated in the usual manner, for example, by dissolving in aqueous sodium hydroxide and precipitating with hydrochloric acid.

Formula IV compounds wherein X is an amino group may also be acylated with an acyl anhydride. Typically about 4 to 6 weights of acyl anhydride and 0.01 to 1 weight of sulfuric acid is used for each weight of Formula IV compound. The reaction temperature may vary from 20° to 60° C., typically 30° C. The reaction is completed in 5 to 20 hours usually about 8 hours. The product is recovered in the usual manner by filtration.

Formula V compounds are prepared by esterifying Formula IV compounds with the appropriate alcohol. Usually a mineral acid such as sulfuric is used as a catalyst in catalytic amounts, i.e., 1% by weight of the Formula IV compound present. Typically about 10 parts by weight of the alcohol is used for each part by weight of the Formula IV compound. The Formula V compounds are isolated in the usual manner, i.e., by cooling and collecting the crystallized solids.

Formula I compounds are then prepared by refluxing the Formula V compound in a suitable solvent, e.g., methanol, if necessary and a polyhydroxyamine. Typically 1 to 3 parts by weight of the polyhydroxyamine and 5 to 7 parts by weight of the solvent is utilized for each part by weight of the Formula V compound. The polyhydroxyamine may also act as a solvent, and then more would be used. Typically 6 to 10 parts by weight per part by weight of Formula V compound is used. Formula I compounds may be recovered in any suitable manner.

Alternatively, compounds of Formula I may be prepared by the following method:

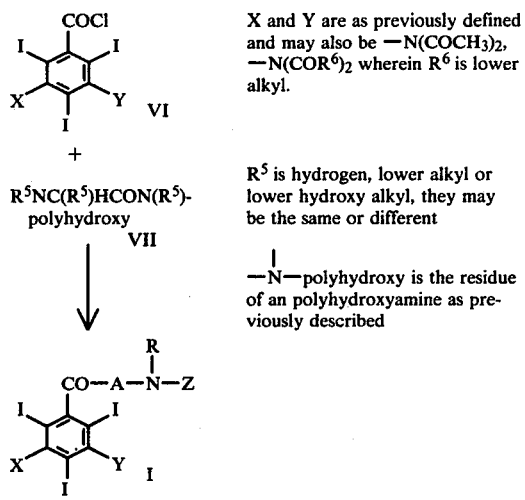

X and Y are as previously defined and may also be —N(COCH$_3$)$_2$, —N(COR$^6$)$_2$ wherein R$^6$ is lower alkyl.

R$^5$ is hydrogen, lower alkyl or lower hydroxy alkyl, they may be the same or different —N—polyhydroxy is the residue of an polyhydroxyamine as previously described Compounds of Formula VI are prepared according to German Pat. No. 2,031,724; Formula VII compounds are prepared according to Liefländer, Hoppe-Seyler's Z. Physicol Chem., 348, 363–70 (1967); and the reaction of VI and VII to form Formula I compound is carried out according to the general method in German Pat. No. 2,031,724.

EXAMPLES

The invention will now be illustrated by the following examples. Temperatures are in degrees C.

EXAMPLE 1

Preparation of 2-(3-Acetamido-2,4,6-triiodo-5-N-methylacetamidobenzoylglycylamino)-2-deoxy-D-glucitol A. Preparation of 2-Acetamido-2-deoxy-D-glucitol

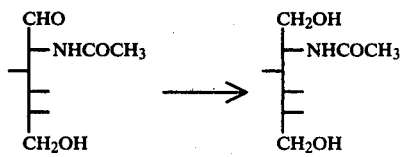

A solution of 100 g. (0.45 mole) of N-acetyl-D-glucosamine in 300 ml. of water was cooled to 15° and a solution of 16 g. of sodium borohydride in 300 ml. of water was added dropwise. During the addition the temperature was held below 50° by addition of ice. After the addition the mixture was stirred for 40 min., cooled to 10° and the excess hydride decomposed by addition of 102 ml. (0.58 mole) of acetic acid. The solution was poured into 550 ml. of prewashed Amberlite 120 resin (H+ form) (0.96 mole @ 1.75 meq/ml.) and stirred for 15 min. The resin was removed by filtration and washed with water. The combined filtrate and wash were evaporated to dryness. The residue was dissolved in 1 l of hot 2β-ethanol, evaporated to 700 ml. and stirred overnight. 90 g. (90%) of product was isolated. The melting point of the product was 153°–154° (lit 153°) and was shown to be pure by tlc (silica gel plate—ethanol/concentrated ammonia 50:50-methanolic sulfuric acid spray and heat development)

B. Preparation of 2-Amino-2-Deoxy-D-Glucitol Hydrochloride

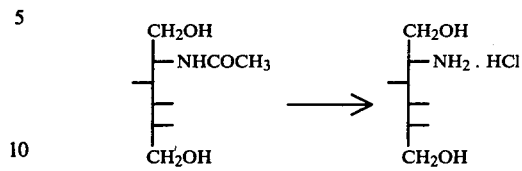

A solution of 90 g. (0.40 mole) of 2-acetamido-2-deoxy-D-glucitol in 1.4 l of water and 0.6 l of conc. hydrochloride acid was heated at 90° for 6 hrs. and allowed to stand overnight at room temperature. The solution was evaporated at aspirator pressure to approximately 1 l. Ethanol was added to the solution in 100 ml. portions and evaporation was continued; the addition and evaporation were repeated until crystals appeared. The solution was allowed to stand for 3 hrs. at room temperature and filtered to furnish 68 g. of product. A second portion 10 g. was isolated from the mother liquor. The melting point of first and second portions were 161° and 160° (lit. 160–161). Both crops were shown to be pure by tlc (silica gel plate—ethanol/concentrated ammonia 50:50—ninhydrin and methanolic sulfuric acid development).

The free 2-amino-2-deoxy-D-glucitol was prepared by stirring 78 g. of the hydrochloride in a mixture of 400 ml. of ethanol and 83 ml. of diethylamine for two days. The solids were filtered and washed with ethanol to give 62 g. (95%) melting point 129°–130° (lit. melting point 131).

C. Preparation of 2-(N-Carbobenzyloxyglycylamino)-2-deoxy-D-glucitol

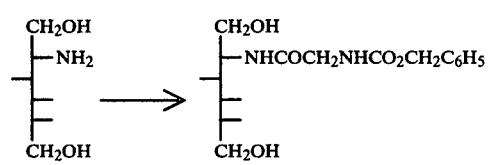

A mixture of 275 ml. of dry tetrahydrofuran and 275 ml. of dry dioxane was cooled to −5° and 12.88 ml. (9.35 g., 0.092 mole) of triethylamine, 8.74 ml. (9.96 g., 0.092 mole) of ethyl chloroformate and 19.23 g. (0.092 mole) of N-carbobenzyloxyglycine were added. The mixture was stirred for 15 min. at −5° and then a cold (0°–5°) solution of 16.65 g. (0.092 mole) of 2-amino-2-deoxy-D-glucitol in 40 ml. of water was added in one portion. The cooling bath was removed and the mixture was allowed to stir at ambient temperature for four hours. The solvent was evaporated in vacuum at 30°–40° and the residue was stirred overnight with 500 ml. of ethanol. Filtration furnished 30 g. of a solid. The solid was recrystallized from 700 ml. of methanol to give 21 g. of product. Tlc shows the product to be pure (silica gel plate—benzene/methyl ketone/88% formic acid 60:25:25—methanolic sulfuric acid development).

D. Preparation of 2-Deoxy-2-glycylamino-D-glucitol Hydrochloride

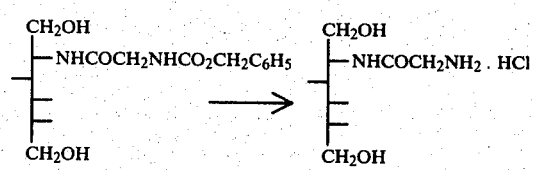

To a solution of 5 g. (0.013 mole) of 2-(N-carbobenzyloxyglycylamino)-2-deoxy-D-glucitol in 90 ml. of water and 10 ml. of acetic acid was added 500 mg. of 5% palladium on charcoal. The mixture was shaken under hydrogen for 16 hours at 50 psi. The catalyst was removed by filtration and 14 ml. of 1 N hydrochloric acid added to the filtrate. The solution was evaporated in vacuum to a gummy residue, which was recrystallized from 2 ml. of water and 100 ml. of ethanol. The crystals, 3.4 g. (0.0125 mole, 92%), melted at 122°–123°. Tlc (cellulose plate—acetonitrile/0.1 N ammonium acetate 60:40—silver nitrate/ammonia or ninhydrin spray development) shows the material to be homogenous.

Analysis calculated for $C_8H_{18}N_2O_6 \cdot HCl \cdot H_2O$: Calculated: C, 32.82; H, 7.23; N, 9.57. Found: C, 33.61; H, 7.37; N, 9.59.

E. Preparation of 2-Deoxy-2-(3-diacetylamino-2,4,6-triiodo-5-N-methylacetamido-benzoylglycylamino)-D-glucitol.

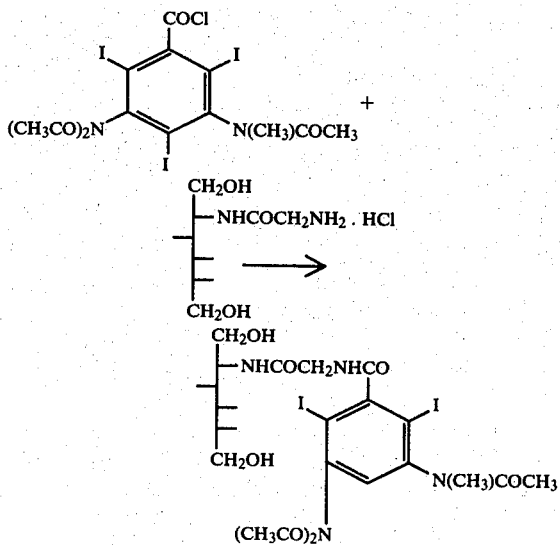

To 90 ml. of dry dimethylformamide at −5° was added 13.77 g. (0.020 mole) of 3-diacetylamino-5-N-methylacetamido-2,4,6-triiodobenzoyl chloride, 6.0 g. (0.022 mole) of 2-deoxy-2-glycylamino-D-glucitol hydrochloride, and 6.08 g. (0.044 mole) of potassium carbonate. The reaction mixture was stirred for three hours at 0° and four days at room temperature. The mixture was filtered and the filtrate evaporated at 55° in vacuum to a gum. The residue was dissolved in 100 ml. of water, brought to pH 4 with hydrochloric acid and stirred overnight with 1 g. of charcoal. The filtered solution was extracted with five, 30 ml. portions of 90% aqueous phenol. The combined phenolic extract was washed with three, 25 ml. portions of water, diluted with 650 ml. of ether and extracted with six, 30 ml. portions of water. The combined aqueous extract was washed with five, 50 ml. portions of ether and evaporated to dryness to yield 17 g. (95%) of crude product.

The crude product was used directly in the next step.

F. Preparation of 2-(3-Acetamido-2,4,6-triiodo-5-N-methylacetamido-benzoylglycylamino)-2-deoxy-D-glucitol.

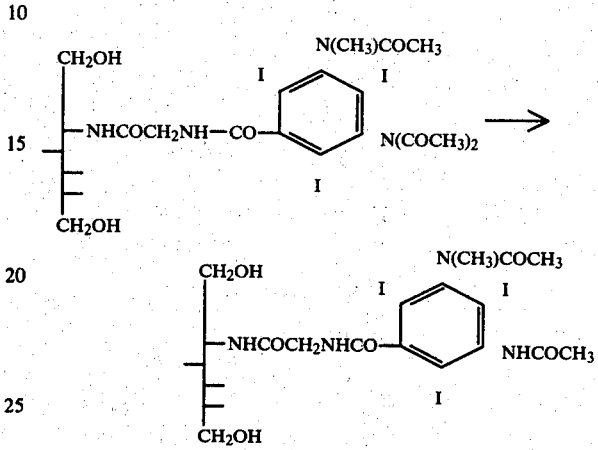

A solution 17 g. (0.019 mole) of 2-deoxy-2-(3-diacetylamino-2,4,6-triiodo-5-N-methylacetamidobenzoylglycylamino)-D-glucitol in 150 ml. of water was adjusted to pH 7 with 1 N sodium hydroxide. The solution was heated to 45° and treated dropwise with 1 N sodium hydroxide until the pH reached 11. Heating was continued and the pH dropped to 10. The addition of 1 N sodium hydroxide was continued keeping the pH at approximately 11. When the pH remained at 10.8 for 5 min., ice was added to cool the solution and the pH was adjusted to 2 with 10% hydrochloric acid. The solution was extracted with six, 25 ml. portions of 90% aqueous phenol. The combined phenolic extract was washed with three, 15 ml. portions of water, was diluted with 800 ml. of ether, and extracted with six 25 ml. portions of water. The combined aqueous extract was washed with six, 25 ml. portions of ether and evaporated to 100 ml. The solution was stirred overnight with 1 g. of charcoal and filtered. The filtrate was extracted with fifteen 20 ml. portions of chloroform/isopropanol—3/1. The aqueous layer was evaporated to remove traces of chloroform and isopropanol and diluted to 150 ml. of water. The solution was continuously extracted with ether for three days. The aqueous layer was evaporated to 100 ml. and and filtered through an ultra filter (0.22μ). Evaporation furnished 10.5 g. of product (melting point—softens 180° C., decomposes about 204° C.). Tlc (silica gel plate—ethyl acetate/methanol/acetic acid 70/30/2 shows the product to be pure. NMR and IR spectra show the product to be consistent with the proposed structure.

Analysis for $C_{20}H_{27}I_3N_4O_9$: Calculated: C, 28.32; H, 3.21; I, 44.89; N, 6.61. Found: C, 28.17; H, 3.20; I, 45.68; N, 6.47.

This compound is approximately 100% soluble in water (w/v).

EXAMPLE 2

Preparation of 2-Deoxy-2-(3-Acetamido-2,4,6-triiodo-5-N-methylcarbamyl-benzoylglycylamino)-D-glucitol

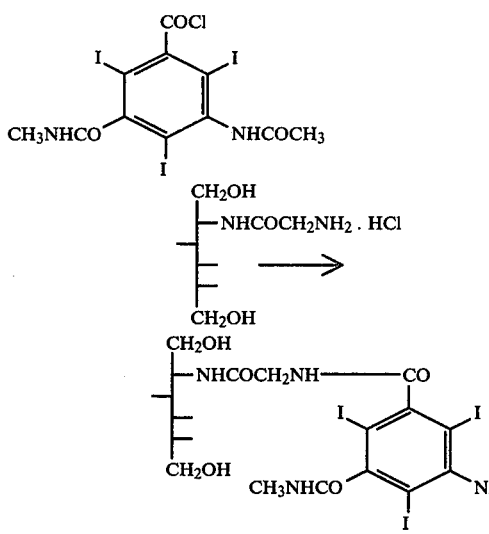

To 300 ml. of dry dimethylformamide at −10° was added 34.85 g. (0.055) of 3-acetamido-5-N-methylcarbamyl-2,4,6-triiodobenzoyl chloride, 16.72 g. (0.121 mole) of anhydrous potassium carbonate and 15 g. (0.061 mole) of 2-deoxy-2-glycylamino-D-glucitol hydrochloride prepared in the same manner as Example 1B. The mixture was stirred at −10° to 0° for 3 hours and at room temperature for four days. The reaction mixture was filtered and the filtrate was evaporated at 50° in vacuo to leave a gummy residue. The residue was stirred with 200 ml. of water and 20 ml. of 1 N hydrochloric acid and filtered to remove undissolved material. The filtrate was extracted with six, 35-ml. portions of 90% aqueous phenol. The combined phenol extract was washed with three, 25-ml. portions of water, was diluted with 750 ml. of ether and was extracted with six, 50 ml. portions of water. The combined aqueous extract was washed with eight, 50 ml. portions of ether and then stirred overnight with 2 g. of charcoal. The charcoal was removed by filtration and the filtrate extracted with twenty, 50 ml. portions of chloroform/isopropanol-3/1. The aqueous layer was evaporated to furnish 20.56 g. of solid material. A seven gram portion of this material was slurried in a mixture of 21 ml. of methanol and 0.5 ml. of conc. ammonia, stirred for 30 min. and filtered. The solids were washed with 13 ml. of methanol and dried to furnish 5.94 g. which was dissolved in 180 ml. of water and stirred overnight with 0.6 g. of charcoal. The solution was filtered, first through a paper filter and then through a 0.22μ filter. Evaporation furnished 5.52 g. of product (36%). Tlc (silica plate-ethyl acetate/methanol/acetic acid 60:40:2) shows the product to be pure. IR and NMR spectra shows the product to be consistent with the proposed structure (melting point—245° darkens, 252°-255° d.)

Analysis for $C_{19}H_{25}I_3N_4O_9$: Calculated: C, 27.36; H, 3.02; I, 45.64; N, 6.72. Found: C, 27.16; H, 3.00; I, 46.33; N, 6.59.

The solubility of this compound in water is approximately 5% (w/v).

EXAMPLE 3

Preparation of (5-Acetamido-2,4,6-triiodoisophthaloyl)-N,N'-bis-2,3-dihydroxypropyl-N,N'-dimethyl-bis glycinamide.

A. Preparation of 5-Amino-2,4,6-triiodoisophthaloyl Chloride

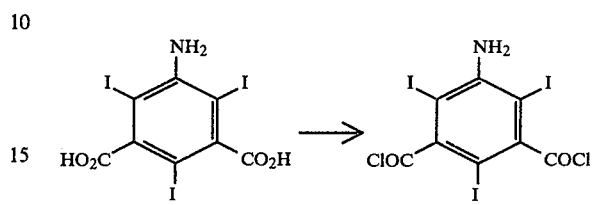

A slurry of 195.2 g. (0.35 mole) of 5-amino2,4,6-triiodoisophthalic acid in 300 ml. of thionyl chloride was refluxed for 24 hours. During the reflux period the solids dissolved. The solution was cooled to 40° and the solvent evaporated to dryness in vacuum. The gummy residue was dissolved in 250 ml. of tetrahydrofuran and evaporated to dryness. The residue was dissolved in 500 ml. of tetrahydrofuran and washed with a mixture of saturated sodium chloride solution and saturated sodium carbonate. The tetrahydrofuran solution was washed twice with saturated sodium chloride solution and dried over anhydrous calcium chloride. The solution was filtered, diluted with 500 ml. of benzene and evaporated to 450 ml. To this solution 450 ml. of petroleum ether (30°-60°) was added dropwise with stirring. After standing for 2 hours the solids were isolated and dried to yield 100.5 g. (48%). The material was pure as shown by tlc (silica plate-benzene/acetone 80/20).

B. Preparation of 5-Acetamido-2,4,6-triiodoisophthaloyl chloride.

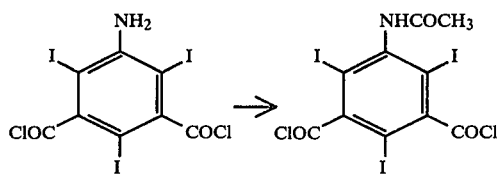

A mixture of 50 ml. of acetic anhydride and 0.1 ml. of conc. sulfuric acid was stirred at room temperature for 5 minutes. To this mixture was added 15 g. (0.025 mole) of 5-amino-2,4,6-triiodoisophthaloyl chloride in one portion and stirring was continued at room temperature for one hour. The mixture was stored overnight at 0°. Filtration furnished 16 g. of solid material. The product was recrystallized from ethyl acetate to furnish 10 g. (63%) of pure product. The compound was shown to be pure by tlc (silica plate-benzene/acetone 80/20).

C. Preparation of 1-Amino-N-glycyl-N-methyl-2,3-propanediol.

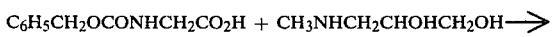

-continued

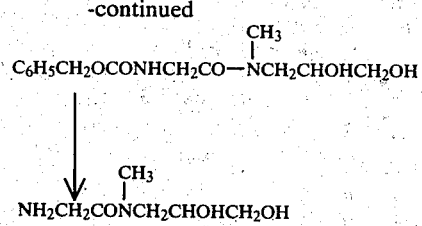

Ethyl chloroformate (0.5 ml., 10.8 g., 0.1 mole), triethylamine (14.2 ml., 10.1 g., 0.1 mole) and N-carbobenzyloxyglycine (20.9 g., 0.1 mole) were added at −5° to a stirring mixture of 150 ml. of dry tetrahydrofuran and 150 ml. of dry dioxane. The mixture was stirred at −5° for 15 minutes and a solution of 10.8 g. of 1-methylamino-2,3-propanediol in 50 ml. of dioxane was added. The cooling bath was removed, and the mixture was allowed to stir at ambient temperature for 16 hours. The white solid in the mixture was removed by filtration and the filtrate was evaporated to a gum. The gum was dissolved in 150 ml. of water and the resulting solution was extracted with eight, 40 ml. portions of methylene chloride. The combined methylene chloride extract was washed with 40 ml. of saturated sodium chloride solution and evaporated to a tacky white solid. The solid was dissolved in 200 ml. of ethanol and evaporated to dryness. The residue was dissolved in 200 ml. of ethanol, 4 g. of 5% palladium on charcoal was added and the mixture shaken under a hydrogen atmosphere for 20 hours at 50 psi. The catalyst was removed by filtration and the solvent evaporated to furnish 12 g. (74%) of nearly pure material. The material was checked by tlc (silica plate-ethanol/conc. ammonium hydroxide 1/1) and used without further purification.

D. Preparation of (5-Acetamido-2,4,6-triiodoisophthaloyl)-N,N'-bis-2,3-dihydroxypropyl-N,N'-dimethyl-bis-glycinamide

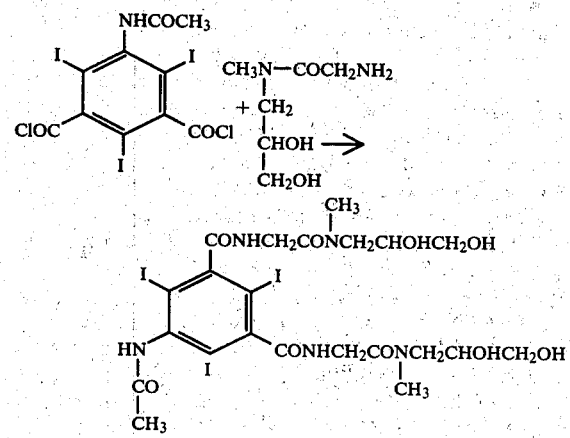

To the 1-amino-N-glycyl-N-methyl-N-methyl-2,3-propanediol, 12 g., slurried in 150 ml. of dry dimethylformamide at 5° was added 15.9 g., (0.025 mole) of 5-acetamido-2,4,6-triiodoisophthaloyl chloride and 6.9 g. (0.05 mole) of anhydrous potassium carbonate. The mixture was stirred at 5°-10° for two hours and at room temperature for five days. The solution was filtered and evaporated at 60°-70° under reduced pressure to furnish a gum. The gum was dissolved in 150 ml. of water, adjusted to pH 1.4 with hydrochloric acid and extracted with five, 30 ml., portions of 90% aqueous phenol. The combined phenol extract was washed with three 20 ml. portions of water, diluted with 800 ml. of ether and extracted with five 40 ml. portions of water. The combined water extract was washed with seven 50 ml. portions of ether and evaporated to furnish 20 g. of crude solid. The solid was chromatographed on 150 g. of silica gel with chloroform/methanol as an elution solvent. Combination of nearly pure fractions furnished 9 g. of product. Rechromatography on silica gel with isobutanol/isopropanol/water as the elution solvent furnished 5 g. of material. The 5 g. was dissolved in water treated with 200 mg. of charcoal overnight and filtered through paper and through a 0.22μ filter. Concentration of the filtrate furnished 5 g. of pure material as shown by tlc (silica gel plate isobutanol/isopropanol/conc. ammonia - 10/4/6), melting point 171°-175° C.

Elemental analysis for $C_{22}H_{30}I_3N_5O_9 \cdot H_2O$: Calculated: C, 29.15; H, 3.34; N, 7.88; I, 42.05. Found: C, 28.84; H, 3.39; N, 7.68; I, 42.67.

The solubility of this compound in water is approximately 100% (w/v).

EXAMPLE 4

Preparation of 5-Acetamido-2,4,6-triiodoisophthaloyl-N,N'-bis-2,3-dihydroxypropyl-N,N'-dimethyl-bis glycinamide.

A. Preparation of N,N'-(5-Acetamido-2,4,6-triiodoisophthaloyl) diglycine dimethyl ester

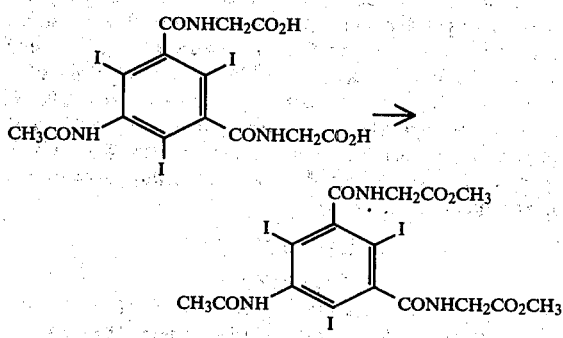

A slurry of 43 g. (60 nM) of N,N'-(5-Acetamido-2,4,6-triiodoisophthaloyl) diglycine in 400 ml. of methanol and 2 ml. of concentrated sulfuric acid was refluxed for 20 hours. The material dissolved after approximately 30 min. of the reflux period and proceeded to precipitate in the reaction solution during the remainder of the reaction time. The reaction mixture was cooled to 10° and filtered. The solids were slurried with 200 ml. of boiling methanol, stirred 30 min., cooled to 10° and filtered to furnish 38.5 g. (51.8 mM, 86%) of the diester. The compound was shown to be pure by tlc (silica gel plate - ethyl/acetate/acetic acid—49/1).

B. Preparation of (5-Acetamido-N,N'-bis-2,3-dihydroxy-propyl-N,N'-dimethyl-2,4,6-triiodoisophthaloyl) bis glycinamide

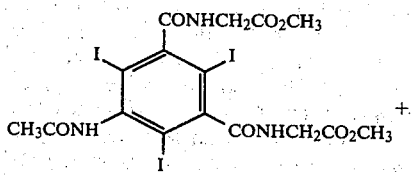

-continued

CH₃NHCH₂CHOHCH₂OH ⟶

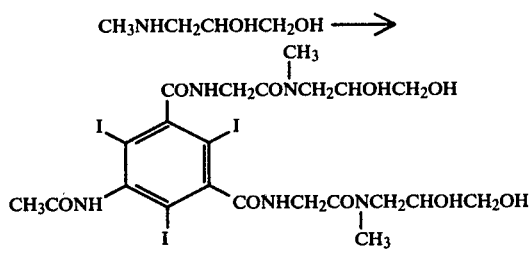

To a solution of 44.9 g. (0.43 mole) of 1-methylamino-2,3-propanediol in 450 ml. of methanol was added 60.0 g. (0.084 mole) of N,N'-(5-acetamido-2,4,6-triiodoisophthaloyl) diglycine dimethyl ester. The slurry was stirred at reflux for two days. The reaction mixture was a clear solution after 36 hours of the reflux period. The reaction mixture was filtered and the filtrate was evaporated to a syrup. The syrup was stirred overnight with 500 ml. of isopropanol and the solids isolated by filtration. The solids were dissolved in 250 ml. of water and stirred for 20 min. with 5 g. of charcoal. The charcoal was removed by filtration and the water was evaporated to furnish 72.5 g. of crude product. The crude product was redissolved in water and treated overnight successively with 5 g. and 10 g. of charcoal. After filtration, the solution was evaporated to dryness. The dry solid was slurried with 400 ml. of isopropyl alcohol stirred for several hours and filtered. The solids were dissolved in water and evaporated to dryness—wt. 43.5 g., yield 58%. The product was shown to be pure by tlc (silica gel plate -isobutanol/isopropanol/conc. ammonia—10/4/6 and chloroform/isopropanol/water—10/25/5). Two spots appeared on the tlc plates. They were separated by column chromatography and shown to be isomers by infra red spectra and NMR spectra. The solubility of these compounds in water is approximately 100% (w/v).

EXAMPLE 5

Preparation of N-(3-Acetamido-2,4,6-triiodo-5-N-methylacetamidobenzoylglycyl)-1-(methylamino)-1-deoxy-D-glucitol

A. Preparation of 3-Acetamido-5-amino-2,4,6-triiodobenzoylglycine

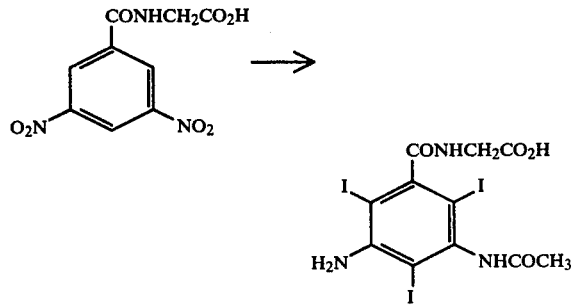

A hydrogenation shaker bottle was charged with 220 ml. of methanol, a slurry of 2 g. of 5% palladium on charcoal in 20 ml. of water, and 26.9 g. (0.1 mole) of 3,5-dinitrohippuric acid. The mixture was shaken under a hydrogen atmosphere for 90 minutes, filtered, and 200 ml. of 1N hydrochloric acid was added to the filtrate. The solution was evaporated to near dryness, the residue was dissolved in 200 ml. of water and 35 ml. of acetic anhydride was added over a 30 min. period. The solution was warmed to 50° and stirred for 30 min. A solution of iodine monochloride, 136 ml. of a 2.42 N solution, was added over 30 min. to the reaction mixture. The mixture was warmed to 75° and stirred at that temperature for 8 hours. The mixture was cooled to room temperature and the solids were isolated. The solids were slurried in water, treated with 10 g. of sodium bisulfite, and reisolated. The solids were dissolved in 300 ml. of water by addition of 50% sodium hydroxide, the pH adjusted to 8 and the solution stirred with 1 g. of charcoal. The slurry was filtered and the filtrate was acidified with 10% hydrochloric acid. The solids were isolated by filtration to yield 32 g. (50%). The product was examined by tlc (silica gel plate—chloroform/methanol/acetic acid—25/2/0.5) and used without further purification.

B. Preparation of 3-Amino-2,4,6-triiodo-5-N-methyl-acetamidobenzoylglycine

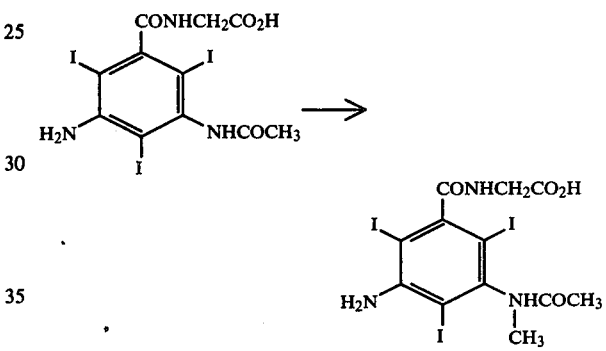

A solution of 32.8 g. (0.052 mole) of 3-acetamido 5-amino-2,4,6-triiodobenzoylglycine in 208 ml. of 0.5 N sodium hydroxide in ethanol was heated at 50° and 13 ml. (29.5 g., 0.208 mole) of methyl iodide was added. The mixture was heated at 50° for 3 hours, cooled to room temperature and brought to pH 9 addition of 1 N aqueous sodium hydroxide. The material in solution was decanted away from an insoluble black tar. The solution was evaporated to a red gum. The gum was dissolved in 200 ml. of water and stirred overnight. The solution was acidified with hydrochloric acid to pH 1, stirred for one hour and filtered to isolate the solids. The solid material was washed with water adjusted to pH 1 with hydrochloric acid to yield, 26.2 g. (78%). The product was pure by tlc (chloroform/methanol/acetic acid—25/2/0.5) and was consistent with the proposed structure as shown by the nuclear magnetic resonance spectra.

C. Preparation of 3-Acetamido-2,4,6-triiodo-5-N-methylacetamidobenzoylglycine

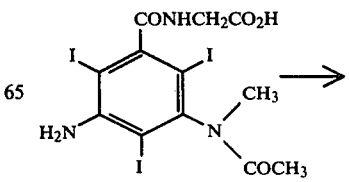

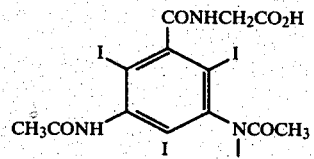

A mixture of 370 ml. of acetic anhydride, 0.5 ml. of conc. sulfuric acid, and 73.9 g. (0.115 mole) of 3-amino-2,4,6-triiodo-5-N-methylacetamido-benzoylglycine was stirred at room temperature. Within 30 minutes, all solids dissolved. After stirring overnight the precipitated solids, 65 g., were isolated and redissolved in 600 ml. of water by adjusting the pH to 9 with 50% aqueous sodium hydroxide. The solution was stirred overnight at room temperature and acidified to pH 1 with 6 N hydrochloric acid. The mixture was cooled to 10° and stirred for 10 minutes, filtered, and the collected solids washed with water. The dried solids were pure as shown by tlc (silica gel plate - chloroform/methanol/acetic acid 25/2/0.5). Yield 52.4 g. (67%). Melting point >260° C. D. Preparation of 3-Acetamido-2,4,6-triiodo-5-N-methlacetamidobenzoylglycine, methyl ester

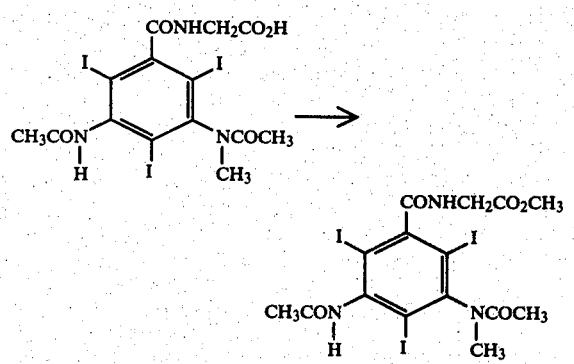

A slurry of 45 g. (0.066 mole) of 3-acetamido-2,4,6-triiodo-5-N-methylacetamidobenzoylglycine in 225 ml. of methanol and 0.2 ml. of conc. sulfuric acid was refluxed for 4 hours. During the reflux period the solids dissolved. The reaction mixture was cooled to room temperature and added dropwise to 2.5.1. of cold ether. The mixture was stirred for 15 minutes, and the solids were isolated by filtration. The solids were washed with four, 200 ml. portions of ether and dried. Yield 38 g. (38%). The product was pure as shown by tlc (silica gel plate - chloroform/methanol/acetic acid—25/2/0.5). Melting point 248°–250° C.

E. Preparation of
N-(3-Acetamido-2,4,6-triiodo-5-N-methylacetamidobenzoylglycyl)-N-methyl-1-amino-1-deoxy-D-glucitol

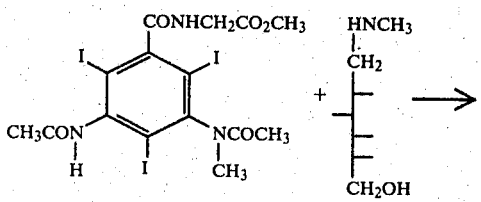

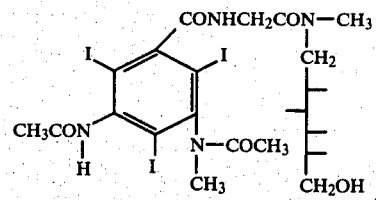

A slurry of 35 g. (0.05 mole) of the methyl ester of 3-acetamido-2,4,6-triiodo-5-N-methylacetamidobenzoylglycine and 29.25 g. (0.15 mole) of 1-deoxy-1-methylamino-D-glucitol in 500 ml. of methanol was refluxed for 3 days. A clear solution resulted during the reflux period. The solvent was evaporated to a gum. The gum was dissolved in 200 ml. of water and evaporated to approximately 175 ml. The solution was diluted with 150 ml. of water and extracted with four, 50 ml. portions of chloroform. The aqueous solution was adjusted to pH 1 with 10% hydrochloric acid and extracted with six, 40 ml. portions of 90% aqueous phenol. The combined phenol extract was washed with three 20 ml. portions of water, diluted with 100 ml. of ether and extracted with six 40 ml. portions of water. The combined aqueous extract was washed with six 50 ml. portions of ether and evaporated to remove traces of ether. The solution was stirred overnight with 3 g. of charcoal, filtered and evaporated to approximately 150 ml. The solution was extracted with sixteen, 50 ml. portions of chloroform/isopropanol—3/1, evaporated to about 100 ml. and filtered through a 0.22μ filter pad. Evaporation furnished 29 g. (67%) of pure material.

Purity was shown by tlc (silica gel plate—isobutanol/isopropanol/conc. ammonia—10/4/6). Structure was confirmed by nuclear magnetic resonance, infrared, and elemental analyses.

Calculated for $C_{21}H_{29}I_3N_4O_9$: Melting point softens 155°, melting point 170°–190° d.

Calculated: C, 28.90; H, 3.48; I, 43.62; N, 6.42. Found: C, 29.40; H, 3.54; I, 42.88; N, 6.64.

This compound is approximately 100% soluble in water (w/v).

EXAMPLE 6

Intravenous, intracerebral and intracisternal acute toxicities of the compounds of Examples 1–5 were determined according to the following procedures. Results are given in Table I below.

Intravenous toxicity study in mice

Swiss albino mice with weights ranging from 18 to 25 grams were used for the performance of the test. Three to four groups of mice with sexes equally represented in each group received single measured doses (mg. of contrast media/kg of body weight) injected into a lateral tail vein at a rate of 1 ml./min.

Following injection, the animals were observed for immediate pharmacological and toxicological manifestations. Mortalities were recorded during the first four hours then daily for seven days. After seven days, surviving animals were sacrificed and necropsies performed.

Calculation of the seven-day $LD_{50}$ value was carried out according to the method of Litchfield and Wilcoxon (J. Pharmacol. Exp. Ther. 96, 99–113, 1949)

Intracerebral toxicity study in mice

Swiss albino mice of either sex, weighing 18 to 23 grams were used for this test according to the method of Haley (Brit. J. Pharmcol. 12, 12-15 1957). At each dose level, the contrast medium was injected as follows. The mouse was grasped firmly by the loose skin behind the head. After the skin was pulled taut, a ⅜ inch 27 gauge needle attached to a 0.25 ml. syringe was inserted perpendicularly through the skull into the brain at a point 2 mm. from either side of the mid line on a line drawn through the anterior base on the ears. A dose of 0.05 ml. (0.1 ml. maximum) of various concentrations of the contrast medium was injected.

Following the injection, the animals were observed for pharmacological and toxicological manifestations. Mortalities were recorded during the first four hours, then daily for two days. Surviving animals were sacrificed 48 hours after injection and the $LD_{50}$ value was calculated according to the method of Litchfield and Wilcoxon (J. Pharmacol. Exp. Ther. 96, 99-113, 1949).

Intracisternal toxicity study in rats

The method of intracisternal administration of contrast media in rats was based on the procedure outlined by Melartin, et al. (Investigative Radiology, Jan. - Feb. 13, 12, 1970). Sprague Dawley rats were anesthetized with ether and positioned on a slanted stand. Following clipping of their hair on the nuchal and cervical area, a small midline incision was made in the skin in the occipital area to facilitate penetration of a 27 gauge needle into the cisterna magna. Aspiration of cerebrospinal fluid indicated that the cisterna magna had been accurately located. Single measured doses of the contrast medium were then injected.

Following injection, the animals were individually housed and observed for pharmacological and toxicological manifestations. Mortalities were recorded during the first four hours, then daily for seven days. Calculation of the $LD_{50}$ value was carried out according to the method of Litchfield and Wilcoxon (J. Pharmacol. Exp. Ther. 96, 99-113, 1949)

TABLE I

| Composition | Intravenous Concentration I W/V | Intravenous $LD_{50}$ mg. I/kg. | Intracerebral Concentration I W/V | Intracerebral $LD_{50}$ mg. I/kg. | Intracisternal Concentration I W/V | Intracisternal $LD_{50}$ mg. I/kg. |
|---|---|---|---|---|---|---|
| Example 1 | 26.3 | *10,000 | 26.3 | *1550 | 35.0 | *525 |
| Example 2 | 11.25 | >7,500 | 11.25 | >543 | 11.25 | <200 |
| Example 3 | 28.2 | >15,000 | 28.2 | *1425 | 14.1 | 100 |
| Example 4 | | | | | | |
| Example 5 | 28.0 | *8,000 | 28.2 | *1100 | 35.0 | 400 |

*approximately

As various changes could be made in the above methods and products without departing from the scope of the invention, it is intended that all matter contained in the above description shall be interpreted as illustrative. It is to be understood therefore that the invention is not limited except as defined by the appended claims.

What is claimed is:

1. A compound of the formula

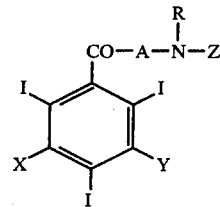

wherein X and Y are each nonionic functions compatible with low toxicity and/or water solubility in the 2,4,6-triiodo configuration, A is an amino substituted lower alkanoic acid coupler and

is a monovalent residue of a polyhydroxy amine, wherein N is a nitrogen atom,

R is hydrogen, lower alkyl, hydroxy-lower alkyl or polyhydroxy lower alkyl, Z is polyhydroxy lower alkyl or oxo polyhydroxy lower alkyl.

2. A compound as set forth in claim 1 wherein R is hydrogen or lower alkyl.

3. A compound as set forth in claim 1 wherein X and Y are each selected from the group consisting of lower alkoxy, hydroxy-(lower alkoxy), lower alkoxy-(lower alkoxy), lower acylamino, lower acylamino-(lower alkyl), lower acylamino-(lower acylamino), hydroxy-lower acylamino, N-(lower alkyl)-lower acylamino, lower alkyl-sulfonamido, N-(lower alkyl)-lower alkyl-sulfonamido, 3,3-bis(lower alkyl)-ureido, lower perfluoroacylamino, carbamyl, N-(lower alkyl) carbamyl, N-(hydroxy lower alkyl) carbamyl, N-(polyhydroxy lower alkyl) carbamyl, N,N-bis-(hydroxy lower alkyl) carbamyl, N,N-bis (polyhydroxy lower alkyl) carbamyl, N,N-di-(lower alkyl) carbamyl, lower alkoxy-(lower acylamino), lower alkoxy-alkoxy(lower acylamino), hydroxy and hydroxy lower alkyl functions.

4. A compound as set forth in claim 2 wherein one of X and Y is hydrogen lower alkoxy, hydroxy-(lower alkoxy), lower alkoxy-(lower alkoxy), lower acylamino, lower acylamino-(lower alkyl), lower acylamino-(lower acylamino), hydroxy-lower acylamino, N-(lower alkyl)-lower acylamino, lower alkylsulfonamido, N-(lower alkyl)-lower alkylsulfonamido, 3,3-bis(lower alkyl)-ureido, lower perfluoroacylamino, carbamyl, N-(lower alkyl) carbamyl, N-(hydroxy lower alkyl) carbamyl, N-(polyhydroxy lower alkyl) carbamyl, N,N-bis-(hydroxy lower alkyl) carbamyl, N,N-bis (polyhydroxy lower alkyl) carbamyl, N,N-di-(lower alkyl) carbamyl, lower alkoxy-(lower acylamino), lower alkoxy-alkoxy(lower acylamino), hydroxy or hydroxy lower alkyl and the other of X and Y is

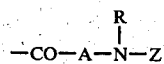

where A, N and Z are as defined above and R is hydrogen or lower alkyl.

5. A compound as set forth in claim 3 wherein X and Y are each selected from the group consisting of lower acylamino, N-(lower alkyl)-lower acylamino, carbamyl, N-(lower alkyl) carbamyl and N,N-di-(lower alkyl) carbamyl.

6. A compound as set forth in claim 1 wherein A is glycyl, R is hydrogen, Z is 2-(1,3,4,5,6-pentahydroxy-D-gluco-hexyl, X is acetamido and Y is N-methylacetamido.

7. A compound according to claim 1 wherein A is glycyl, R is hydrogen, Z is 2-(1,3,4,5,6-pentahydroxy-D-gluco-hexyl), X is acetamido and Y is methylcarbamyl.

8. A compound according to claim 1 wherein A is glycyl, R is methyl, Z is 2,3-dihydroxypropyl, X is acetamido, and Y is

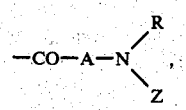

wherein A is glycyl, R is methyl, and Z is 2,3-dihydroxypropyl.

9. A compound according to claim 1 wherein A is glycyl, R is methyl, Z is 1-(2,3,4,5,6-pentahydroxy-D-gluco hexyl), X is acetamido, and Y is N-methylacetamido.

10. A radiological composition containing a compound of claim 1 in a sufficient amount to provide satisfactory x-ray visualization together with a pharmaceutically acceptable radiological vehicle.

11. In a method for X-ray visualization wherein a radiological composition containing an X-ray contrast agent in a pharmaceutically acceptable radiological carrier is injected in a sufficient amount to provide adequate visualization and thereafter X-ray visualization carried out, the improvement comprising using as the radiological composition a composition containing a compound of claim 1 in a sufficient amount to provide satisfactory X-ray visualization together with a pharmaceutically acceptable radiological vehicle suitable for injection.

12. A compound as set forth in claim 2 wherein said monovalent residue is a residue selected from the group consisting of aldosamines, N-(lower alkyl) aldosamines, ketosamines, N-(lower alkyl) ketosamines, N-(polyhydroxy-lower alkyl) amines, N-alkyl-N-(polyhydroxy-lower alkoxy alkyl) amines, and deoxy-aldosamines.

13. A compound as set forth in claim 12 wherein A is glycyl.

14. A radiological composition containing the compound of claim 6 in a sufficient amount to provide satisfactory X-ray visualization together with a pharmaceutically acceptable radiological vehicle.

15. A radiological composition containing the compound of claim 7 in a sufficient amount to provide satisfactory X-ray visualization together with a pharmaceutically acceptable radiological vehicle.

16. A radiological composition containing the compound of claim 8 in a sufficient amount to provide satisfactory X-ray visualization together with a pharmaceutically acceptable radiological vehicle.

17. A radiological composition containing the compound of claim 9 in a sufficient amount to provide satisfactory X-ray visualization together with a pharmaceutically acceptable radiological vehicle.

18. A radiological composition containing a compound of claim 12 in a sufficient amount to provide satisfactory X-ray visualization together with a pharmaceutically acceptable radiological vehicle.

19. In a method for X-ray visualization wherein a radiological composition containing an X-ray contrast agent in a pharmaceutically acceptable radiological carrier is injected in a sufficient amount to provide adequate visualization and thereafter X-ray visualization carried out, the improvement comprising utilizing as the radiological composition a composition containing a compound of claim 12 in a sufficient amount to provide satisfactory X-ray visualization together with a pharmaceutically acceptable radiological vehicle suitable for injection.

20. In a method for X-ray visualization wherein a radiological composition containing an X-ray contrast agent in a pharmaceutically acceptable radiological carrier is injected in a sufficient amount to provide adequate visualization and thereafter X-ray visualization is carried out, the improvement comprising utilizing as the radiological composition a composition containing the compound of claim 6 in a sufficient amount to provide satisfactory X-ray visualization together with a pharmaceutically acceptable radiological vehicle suitable for injection.

21. In a method for X-ray visualization wherein a radiological composition containing an X-ray contrast agent in a pharmaceutically acceptable radiological carrier is injected in a sufficient amount to provide adequate visualization and thereafter X-ray visualization carried out, the improvement comprising utilizing as the radiological composition a composition containing the compound of claim 7 in a sufficient amount to provide satisfactory X-ray visualization together with a pharmaceutically acceptable radiological vehicle suitable for injection.

22. In a method for X-ray visualization wherein a radiological composition containing an X-ray contrast agent in a pharmaceutically acceptable radiological carrier is injected in a sufficient amount to provide adequate visualization and thereafter X-ray visualization carried out, the improvement comprising utilizing as the radiological composition a composition containing the compound of claim 8 in a sufficient amount to provide satisfactory X-ray visualization together with a pharmaceutically acceptable radiological vehicle suitable for injection.

23. In a method for X-ray visualization wherein a radiological composition containing an X-ray contrast agent in a pharmaceutically acceptable radiological carrier is injected in a sufficient amount to provide adequate visualization and thereafter X-ray visualization carried out, the improvement comprising utilizing as the radiological composition a composition containing the compound of claim 9 in a sufficient amount to provide satisfactory X-ray visualization together with a pharmaceutically acceptable radiological vehicle suitable for injection.

24. A compound as set forth in claim 3 wherein one of X and Y is a lower acylamino, lower acylamino-(lower acylamino), hydroxy-lower acylamino, N-(lower alkyl)-lower acylamino, lower alkoxy-(lower acylamino) or lower alkoxy-alkoxy(lower acylamino) group and the other of X and Y is a lower acylamino, lower acylamino-(lower acylamino), hydroxy-lower acylamino, N-(lower alkyl)-lower acylamino, lower alkoxy-(lower acylamino), lower alkoxy-alkoxy(lower acylamino), carbamyl, N-(lower alkyl) carbamyl, N-(hydroxy lower alkyl) carbamyl, N-(polyhydroxy lower alkyl) carbamyl, N,N-bis-(hydroxy lower alkyl) carbamyl, N,N-bis-(hydroxy lower alkyl) carbamyl, N,N-bis-(polyhydroxy lower alkyl) carbamyl or N,N-di-(lower alkyl) carbamyl group.

25. A compound as set forth in claim 24 wherein

is the monovalent rsidue of an aldosamine having the formula CHO—(CHOH)$_n$—CHNH$_2$—(CHOH)$_m$—CH$_2$OH where m is 0 to 4, n is 0 to 4 and the sum of m+n is 0 to 4; a N-lower alkyl aldosamine having the formula CHO—(CHOH)$_n$—CHNHR—(CHOH)$_m$—CH$_2$OH where m is 0 to 4, n is 0 to 4, the sum of m+n is 0 to 4 and R is lower alkyl; a N-(polyhydroxy-lower alkyl) amine having the formula H—(CHOH)$_n$—CHNH$_2$—(CHOH)$_m$—CH$_2$OH where n is 0 to 5, m is 0 to 5 and the sum of n+m is 0 to 5; or a N-lower alkyl-N-(polyhydroxy lower alkyl) amine having the formula H—(CHOH)$_n$—CHNHR—(CHOH)$_m$—CH$_2$OH where n is 0 to 2, m is 1 to 5, the sum of m+n is 1 to 5 and R is lower alkyl.

26. A compound as set forth in claim 25 wherein one of X and Y is lower acylamino, or N-(lower alkyl)-lower acylamino and the other of X and Y is lower acylamino, N-(lower alkyl)-lower acylamino, carbamyl, N-(lower alkyl) carbamyl, N,N di-(lower alkyl) carbamyl, or N(hydroxy lower alkyl) carbamyl.

27. A compound as set forth in claim 26 wherein A is glycyl.

28. A radiological composition containing the compound of claim 25 in a sufficient amount to provide satisfactory x-ray visualization together with a pharmaceutically acceptable radiological vehicle.

29. A radiological composition containing the compound of claim 26 in a sufficient amount to provide satisfactory x-ray visualization together with a pharmaceutically acceptable radiological vehicle.

30. In a method for x-ray visualization wherein a radiological composition containing an x-ray contrast agent in a pharmaceutically acceptable radiological carrier is injected in a sufficient amount to provide adequate visualization and thereafter x-ray visualization carried out, the improvement comprising utilizing as the radiological composition a composition containing the compound of claim 25 in a sufficient amount to provide satisfactory x-ray visualization together with a pharmaceutically acceptable radiological vehicle suitable for injection.

31. In a method for x-ray visualization wherein a radiological composition containing an x-ray contrast agent in a pharmaceutically acceptable radiological carrier is injected in a sufficient amount to provide adequate visualization and thereafter x-ray visualization carried out, the improvement comprising utilizing as the radiological composition a composition containing the compound of claim 26 in a sufficient amount to provide satisfactory x-ray visualization together with a pharmaceutically acceptable radiological vehicle suitable for injection.

32. A compound as set forth in claim 4 wherein one of X and Y is lower acylamino, lower acylamino-(lower acylamino), hydroxy-lower acylamino, N-(lower alkyl)-lower acylamino, lower alkoxy-(lower acylamino) or lower alkoxy-alkoxy (lower acylamino).

33. A compound as set forth in claim 32 wherein A is glycyl.

34. A radiological composition containing the compound of claim 4 in a sufficient amount to provide satisfactory x-ray visualization together with a pharmaceutically acceptable radiological vehicle.

35. A radiological composition containing the compound of claim 32 in a sufficient amount to provide satisfactory x-ray visualization together with a pharmaceutically acceptable radiological vehicle.

36. In a method for x-ray visualization wherein a radiological composition containing an x-ray contrast agent in a pharmaceutically acceptable radiological carrier is injected in a sufficient amount to provide adequate visualization and thereafter x-ray visualization carried out, the improvement comprising utilizing as the radiological composition a composition containing the compound of claim 4 in a sufficient amount to provide satisfactory x-ray visualization together with a pharmaceutically acceptable radiological vehicle suitable for injection.

37. In a method for x-ray visualization wherein a radiological composition containing an x-ray contrast agent in a pharmaceutically acceptable radiological carrier is injected in a sufficient amount to provide adequate visualization and thereafter x-ray visualization carried out, the improvement comprising utilizing as the radiological composition a composition containing the compound of claim 32 in a sufficient amount to provide satisfactory x-ray visualization together with a pharmaceutically acceptable biological vehicle suitable for injection.

* * * * *